United States Patent [19]

Bernauer et al.

[11] 4,230,623
[45] Oct. 28, 1980

[54] PYRROLIDINE DERIVATIVES

[75] Inventors: Karl Bernauer, Oberwill; Karlheinz Pfoertner; Fernand Schneider, both of Basel, all of Switzerland; Hans Schmid, deceased, late of Schwerzenbach, Switzerland, by Käthe Anna Schmid-Appenzelier, heir; by Mary Margrith Baumann-Schmid, heir, Niedergösgen; by Maria Albertine Schmid-Suter, heir, Gränichen, both of Switzerland; by Jeannette Martha Wawrla-Schmid, heir, Nüziders, Austria; by Ernst Georges Schmid-Gautschi, heir, Niedergösgen, Switzerland

[73] Assignee: Hoffmann-La Roche Inc., Nutley, N.J.

[21] Appl. No.: 960,352

[22] Filed: Nov. 13, 1978

Related U.S. Application Data

[63] Continuation-in-part of Ser. No. 816,974, Jul. 19, 1977, abandoned.

[51] Int. Cl.$^3$ .............................................. C07D 207/44
[52] U.S. Cl. ......................... 260/326.5 SM; 424/274
[58] Field of Search .............................. 260/326.5 SM Primary Examiner—Jose Tovar
Attorney, Agent, or Firm—Jon S. Saxe; George M. Gould; Peter R. Shearer

[57] ABSTRACT

Pyrrolidine derivatives of the formula

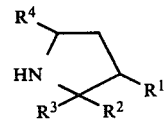

wherein $R^1$, $R^2$, $R^3$ and $R^4$ are as hereinafter described, prepared inter alia from the corresponding pyrrolines, are described. The compounds are useful as analgesic agents.

2 Claims, No Drawings

PYRROLIDINE DERIVATIVES

This is a continuation-in-part of applicant's copending U.S. patent application Ser. No. 816,974, filed July 19, 1977, which is now abandoned.

BRIEF SUMMARY OF THE INVENTION

The pyrrolidine derivatives of the invention can be characterized by the formula

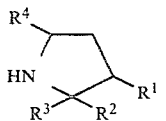

I wherein $R^1$ is 2-thienyl or phenyl substituted by a tertiary amino group, $R^2$ and $R^3$, independently, are hydrogen or lower alkyl, and $R^4$ is phenyl or phenyl substituted by halogen, lower alkyl, lower alkoxy, nitro, amino or a secondary or tertiary amino group, with the proviso that $R^1$ is phenyl substituted by a tertiary amino group, when $R^4$ is phenyl or halo-substituted phenyl,
or isomers thereof, or a pharmaceutically acceptable acid addition salt thereof. The compounds of formula I are useful as analgesic agents.

DETAILED DESCRIPTION OF THE INVENTION

Preferred pyrrolidine derivatives of the invention are those compounds of formula I wherein $R^1$ is 2-thienyl or a pharmaceutically acceptable acid addition salt thereof. Compounds of formula I wherein $R^2$ and $R^3$ are each methyl as well as pharmaceutically acceptable acid addition salts thereof, are also preferred. Compounds of formula I wherein $R^4$ is p-methoxyphenyl as well as the pharmaceutically acceptable acid addition salts thereof are also preferred. 5-(p-Methoxyphenyl)-2,2-dimethyl-3-(2-thienyl)-pyrrolidine in its isomeric forms, especially in the cis form, or pharmaceutically acceptable acid addition salts thereof are especially preferred.

The pyrrolidine derivatives of the invention, i.e., the compounds of the formula

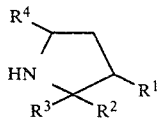

I wherein $R^1$ is 2-thienyl or phenyl substituted by a tertiary amino group, $R^2$ and $R^3$, independently, are hydrogen or lower alkyl, and $R^4$ is phenyl or phenyl substituted by halogen, lower alkyl, lower alkoxy, nitro, amino or a secondary or tertiary amino group, with the proviso that $R^1$ is phenyl substituted by a tertiary amino group, when $R^4$ is phenyl or halo-substituted phenyl,
or a pharmaceutically acceptable acid addition salt thereof, can be prepared by reducing a compound of the formula

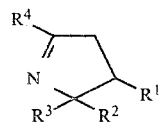

II wherein $R^1$, $R^2$, $R^3$ and $R^4$ are as previously described, or an N-oxide thereof, if desired, nitrating a phenyl group denoted by $R^4$, if desired, converting a base obtained into a pharmaceutically acceptable acid addition salt, if desired, separating a mixture of cis and trans isomer which may be obtained, and, also if desired, splitting a racemate obtained into the optical antipodes.

As used in this specification, the term "lower alkyl" denotes a straight-chain or branched-chain alkyl containing up to 7 carbon atoms, for example, methyl, ethyl, propyl, isopropyl, butyl, pentyl, hexyl, heptyl, or the like; methyl is preferred. The term "halogen" denotes fluorine, chlorine, bromine and iodine; chlorine is preferred. The term "lower alkoxy" denotes an alkoxy group containing up to 7 carbon atoms, for example, methoxy, ethoxy, propoxy, butoxy or the like; methoxy is preferred. The term "secondary amino" denotes an amino group bearing a lower aliphatic substituent, for example, lower alkyl group. Exemplary of such groups are methylamino, ethylamino, propylamino, butylamino, or the like. The term "tertiary amino" denotes an amino group bearing two lower aliphatic substituents, for example, lower alkyl groups, or denotes the residue of a 5-membered or 6-membered saturated N-heterocyclic ring which may contain an additional nitrogen, oxygen or sulfur, and which may also be substituted, for example, lower alkyl or hydroxy-(lower alkyl). Exemplary of the 5-membered or 6-membered saturated N-heterocyclic ring are pyrrolidinyl, piperidinyl, morpholinyl, thiomorpholinyl, piperazinyl, picolinyl, N'-methyl-piperazinyl, N'-hydroxy-ethyl-piperazinyl, or the like.

The compounds of formula I contain at least one basic nitrogen and can therefore form acid addition salts with pharmaceutically acceptable inorganic and organic acids. Exemplary of such acids are hydrochloric acid, hydrobromic acid, sulfuric acid, acetic acid, succinic acid, maleic acid, ethanesulfonic acid, p-toluenesulfonic acid or the like. The hydrochloride salts are especially preferred.

The salts of the compounds of formula I can also exist as hydrates, for example, as monohydrates or polyhydrates, such as trihydrates.

The reduction of a compound of formula II can be carried out catalytically using a noble metal catalyst, such as platinum, or using a Raney-nickel catalyst. When a Raney-nickel catalyst is used, the reduction is conveniently carried out under an elevated pressure, for example, under a pressure of more than 2 atmospheres. When the reduction is carried out utilizing the aforementioned reducing agents, the compounds of formula I are formed predominantly in the cis form, that is, up to more than 90%.

The reduction of a compound of formula II, however, can also be carried out utilizing nascent hydrogen, prepared by the reaction of acids on metals. The hydrogen can be generated, for example, by the action of a lower alkanecarboxylic acid, preferably formic acid, on zinc, especially zinc dust, or on iron, especially iron powder. The reduction with zinc or iron and acid can be carried out at a temperature between about 0° C. and about 80° C., preferably at about 60° C. When the reduction is carried out according to this procedure, the compounds of formula I are formed predominantly in the trans configuration.

The reduction of a compound of formula II can, however, also be carried out using complex hydries (e.g. sodium boronhydride or lithium aluminium hydride). When the reduction is carried out according to this procedure, the compounds of formula I are formed predominantly in the cis configuration.

When a compound of formula I is prepared from a compound of formula II wherein $R^4$ is a nitro-substituted phenyl, then the nitro group is converted into the amino group during the reduction.

When a compound of formula I wherein $R^4$ is a nitro-substituted phenyl group is desired, then the nitro group is subsequently introduced on the phenyl group. Such substitution can be carried out using a nitrating agent, such as nitric acid. The nitration is conveniently carried out utilizing a mixture of concentrated nitric acid and concentrated sulfuric acid, preferably with cooling.

A pharmaceutically acceptable acid addition salt of a compound of formula I can be obtained from a compound of formula I by treatment with an appropriate acid.

A mixture of the cis and trans isomers of a compound of formula I which may be obtained can be separated, if desired, into the individual isomers, for example, by fractional crystallization. The cis isomers are especially preferred.

The isomer obtained, which is not preferred, can be isomerized, if desired, via a compound of formula II. The isomerization can be carried out not only on the isomer mixture but also after the separation of the mixture. This isomerization comprises a dehydrogenation and a subsequent hydrogenation. The dehydrogenation can be carried out, for example, with N-halogenation, preferably N-chlorination, for example, with an alkali metal hypochlorite, and subsequent cleavage of hydrogen halide using a base, for example, sodium methylate. The thus-obtained pyrroline is then reduced to the desired isomers of formula I as described earlier.

A racemate obtained can be split into the optical antipodes using, for example, an optically active acid, such as dibenzoyltartaric acid, camphorsulfonic acid, or the like.

In a preferred embodiment of the foregoing process, a starting material wherein $R^1$ is 2-thienyl is utilized. In another preferred embodiment, a starting material wherein each of $R^2$ and $R^3$ is methyl is utilized. In another preferred embodiment, a starting material wherein $R^4$ is p-methoxyphenyl is utilized. In a more preferred embodiment, 5-(p-methoxyphenyl)-2,2-dimethyl-3-(2-thienyl)-pyrrolidine, especially in the cis form, or a pharmaceutically acceptable acid addition salt thereof is prepared.

The compounds of formula II and their acid addition salts and N-oxides are novel and they also form part of the present invention. The compounds of formula II can be prepared by cyclizing a compound of the formula

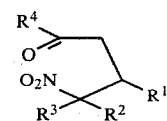

wherein $R^1$, $R^2$, $R^3$ and $R^4$ are as previously described, under reducing conditions and, if desired, converting a resulting compound of formula II into an N-oxide or into an acid addition salt. The compounds of formula III are known.

The starting materials of formula III can be prepared by aldol condensation of a compound of the general formula

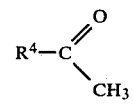

wherein $R^4$ is as previously described with a compound of the general formula

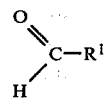

wherein $R^1$ is as previously described to yield a compound of the general formula

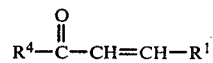

wherein $R^1$ and $R^4$ are as previously described.

The compound of formula VI is reached with a nitro compound of the general formula

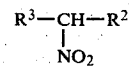

wherein $R^2$ and $R^3$ are as previously described to yield the compound of formula III. All these steps can be performed according to known methods and especially according to example 1.

The compounds of formulae IV, V, VI and VII are either known or can be prepared in a manner known per se.

The reductive cyclization of a compound of formula III can be carried out utilizing tin and glacial acetic acid, preferably at the boiling point of the mixture. Depending on the conditions utilized, a compound of formula II or an N-oxide thereof is obtained.

The reductive cyclization of a compound of formula III to obtain a compound of formula II can also be carried out under specific conditions utilizing zinc and a lower alkanecarboxylic acid, preferably formic acid. However, in this case, when a further reduction to a compound of formula I is to be prevented, it is necessary to use a small amount of zinc and short reductive cyclization times. The compounds of formula II are also obtained by decreasing the amount of acid or lowering the temperature.

The compounds of formula II prepared according to either of the foregoing procedures can be converted in a known manner into acid addition salts or into N-oxides. The N-oxides can be prepared, for example, by treating a compound of formula II with a peracid or hydrogen peroxide.

In the process of the invention, the starting materials of formula II need not be used in an isolated form; particularly since they cannot in all instances be isolated. On the contrary, it is possible to obtain a compound of formula I directly during the reductive cyclization of a compound of formula III.

The pyrrolidine derivatives of formula I of the present invention have pharmacodynamic activity and can, accordingly, be utilized as the active ingredient in pharmaceutical preparations. The compounds of formula I can be used as medicaments in the form of pharmaceutical preparations which contain them in association with a compatible pharmaceutical carrier material. Such carrier material can be an organic or inorganic inert carrier material suitable for enteral or parenteral administration, for example, water, gelatin, lactose, starch, magnesium stearate, talc, vegetable oils, gums, polyalkyleneglycols, or the like. The pharmaceutical preparations can be made up in solid form, for example, as tablets, dragees, suppositories, or capsules, or in liquid form, for example, as solutions, suspensions or emulsions. The pharmaceutical preparations may be sterilized and/or may contain adjuvants, such as preserving, stabilizing, wetting or emulsifying agents, salts for varying the osmotic pressure or buffers. They can also contain other therapeutically active substances.

The pyrrolidine derivatives of formula I of the invention have analgesic activity without being addictive. Therefore, they are useful as analgesic agents for the control of pain. For example, racemic cis-5-(p-methoxyphenyl)-2,2-dimethyl-3-(2-thienyl)-pyrrolidine hydrochloride exhibits an $ED_{50}$ of 30 mg/kg. (60 minutes) in the writhing test following oral administration to mice. The acute peroral toxicity of racemic cis-5-(p-methoxyphenyl)-2,2-dimethyl-3-(2-thienyl)-pyrrolidine hydrochloride has been demonstrated to be 250–500 mg/kg (24 hour value) in mice. An $ED_{50}$ of 153 (60 minutes) mg/kg has been exhibited by racemic cis-5-(p-methoxyphenyl)-2,2-dimethyl-3-(2-thienyl)-pyrrolidine hydrochloride in the hot-plate test.

The compounds of formula I and their pharmaceutically acceptable acid addition salts can be administered to warm-blooded animals in individual doses in the range of from about 50 to about 200 mg., one to three times daily. Oral administration is preferred.

The following Examples further illustrate the invention. All temperatures are in degrees Centigrade, unless otherwise mentioned.

EXAMPLE 1

Preparation of cis-5-(p-methoxyphenyl)-2,2-dimethyl-3-(2-thienyl)-pyrrolidine hydrochloride 17 G. of 2-(p-methoxyphenyl)-5,5-dimethyl-4-(2-thienyl)-1-pyrroline are dissolved in 250 ml. of absolute ethanol and treated with 10 g. of sodium borohydride. The mixture is stirred for a further 6 hours under a nitrogen atmosphere, evaporated under reduced pressure, the residue taken up in water and extracted with ether. The organic phase is dried over sodium sulfate and evaporated under reduced pressure. The residual pyrrolidine is dissolved in ethanol and converted by the addition of concentrated hydrochloric acid into the hydrochloride. The latter is crystallized from acetone/diisopropyl ether after removal of the solvent under reduced pressure. There is obtained cis-5-(p-methoxyphenyl)-2,2-dimethyl-3-(2-thienyl)-pyrrolidine hydrochloride, having a melting point of 181° C.

The 2-(p-methoxyphenyl)-5,5-dimethyl-4-(2-thienyl)-1-pyrroline used as the starting material can be prepared as follows:

180 G. of zinc powder are added portionwise while stirring over a period of 5 hours to a solution of 194 g. of 4'-methoxy-4-methyl-4-nitro-3-(2-thienyl)-valerophenone in 400 ml. of ethanol and 400 ml. of formic acid. The temperature is held at 48°–50° C. during this addition. The zinc sludge is then filtered off and the filtrate strongly concentrated under reduced pressure. The residue is taken up in water and made alkaline with 3-N sodium hydroxide. The mixture is extracted with methylene chloride, the organic phase washed with water, dried over sodium sulfate and evaporated under reduced pressure. The oily residue is chromatographed on silica gel, elution being carried out firstly with pure benzene and then with benzene/acetone mixtures with increasing acetone content (up to 50% acetone). There is obtained 2-(p-methoxy-phenyl)-5,5-dimethyl-4-(2-thienyl)-1-pyrroline which melts at 84° C. after recrystallization from n-hexane.

The 4'-methoxy-4-methyl-4-nitro-3-(2-thienyl)-valerophenone starting material can be preferred as follows:

(a) 300 g of acetanisole (4-methoxyacetophenone) and 300 ml of thienyl-2-acetaldehyde are finely divided in 2 l of water whilst vigorous stirring after which 200 ml of a 10% sodium hydroxide solution are added thereto. The emulsion is stirred over a period of 60 hours at ambient temperature under nitrogen. After extraction with ether, the organic phase is dried over sodium sulfate and the solvent is evaporated off. The remaining brown oil is distilled under high vacuum. The distillate solidifies and it crystallises from methanol. There is obtained 4-methoxy-3-(2-thienyl)acrylophenone of melting point 104° C.

(b) 168 g of 4-methoxy-3-(2-thienyl)-acrylophenone are heated to the boiling point together with 267 g of 2-nitropropane and 400 ml of absolute methanol. A solution of 43 g of sodium methylate in absolute methanol is added within 60 minutes. The resulting mixture is still refluxed during 3 hours. After cooling 43 g of glacial acetic acid are added to the reaction mixture, which is then evaporated to dryness. The residue is taken up with 1500 ml of dichloromethane. This solution is twice washed with 500 ml of water each time, dried over sodium sulfate and evaporated to dryness. The residue crystallises from ethanol and yields 4'-methoxy-4-methyl-4-nitro-3-(2-thienyl)-valerophenone of melting point 90° C.

EXAMPLE 2

Preparation of trans-3-(p-dimethylaminophenyl)-2,2-dimethyl-5-phenyl-pyrrolidine 47 G. of 4-(p-dimethylaminophenyl)-5,5-dimethyl-2-phenyl-1-pyrroline 1-oxide are dissolved in a mixture of 400 ml. of ethanol and 400 ml. of formic acid and treated portionwise while stirring with 80 g. of zinc powder. The temperature is held at 43° C. during this addition. Subsequently, the mixture is stirred for a further 2 hours, the zinc sludge is then filtered off and the filtrate evaporated under reduced pressure. The residue is taken up in water, neutralized with 3-N sodium hydroxide and extracted with ether. The ether phase is then dried over sodium sulfate and evaporated under reduced pressure. The residue is chromatographed on silica gel, elution being carried out first with pure benzene and then with benzene/acetone mixtures with increasing acetone content (up to 50% acetone). There is thus obtained trans-3-(p-dimethylaminophenyl)-2,2-dimethyl-5-phenyl-pyrrolidine which melts at 108°–109° C. after crystallization from n-hexane.

In the chromatography there is also obtained 5,5-dimethyl-2-phenyl-4-(p-dimethylaminophenyl)-1-pyrroline which is further processed as described in Example 3 hereinafter.

The 4-(p-dimethylaminophenyl)-5,5-dimethyl-2-phenyl-1-pyrroline 1-oxide used as the starting material can be prepared as follows:

120 G. of 4-methyl-4-nitro-3-(p-dimethylaminophenyl)-valerophenone are dissolved in a mixture of 1 l. of ethanol and 1 l. of formic acid. 50 G. of zinc powder are added portionwise to this solution while stirring over a period of 8 hours, care being taken that the temperature does not exceed 58° C. The mixture is stirred for a further 12 hours and treated in the same manner with 50 g. of zinc powder. Subsequently, the zinc sludge is filtered off, the filtrate diluted with water and neutralized with sodium hydroxide while cooling with ice. The mixture is extracted with methylene chloride, the organic phase dried over sodium sulfate and the solvent removed under reduced pressure. The residue is boiled at reflux for a short time in high-boiling petroleum ether (fraction 80°–105° C.). It is then decanted from the non-dissolved dark oil and the petroleum ether solution decolorized with active carbon. 4-(p-Dimethylaminophenyl)-5,5-dimethyl-2-phenyl-1-pyrroline 1-oxide crystallizes upon cooling.

EXAMPLE 3

Preparation of cis-3-(p-dimethylaminophenyl)-2,2-dimethyl-5-phenyl-pyrrolidine

16 G. of 5,5-dimethyl-2-phenyl-4-(p-dimethylaminophenyl)-1-pyrroline are dissolved in 300 ml. of absolute ethanol and treated with 16 g. of sodium borohydride. The solution is stirred under nitrogen at room temperature for 14 hours. It is subsequently evaporated to dryness under reduced pressure and the residue suspended in water by intensive stirring. The non-dissolved constituent is filtered off, dried and recrystallized, first from n-hexane and then from diisopropyl ether. There is obtained cis-3-(p-dimethylaminophenyl)-2,2-dimethyl-5-phenyl-pyrrolidine, having a melting point of 117°–118° C.

EXAMPLE 4

Preparation of cis-3-(p-dimethylaminophenyl)-2,2-dimethyl-5-(p-methoxyphenyl)-pyrrolidine dihydrochloride A solution of 7 g. of 2-(p-methoxyphenyl)-5,5-dimethyl-4-(p-dimethylaminophenyl)-1-pyrroline hydrochloride in water is made alkaline with 3-N sodium hydroxide and extracted with methylene chloride. The organic phase is washed with water and dried over sodium sulfate. The oil which remains after removal of the solvent is taken up in 150 ml. of absolute ethanol and the solution treated with 5 g. of sodium borohydride. The mixture is then stirred at room temperature for 12 hours under nitrogen. Subsequently, the mixture is evaporated to dryness under reduced pressure and the residue suspended in water by intensive stirring. The non-dissolved constituent is filtered off, dried and recrystallized from n-pentane. The thus-purified base is taken up in ethanolic hydrochloric acid, again evaporated to dryness under reduced pressure and the residue recrystallized from ethanol/acetone. There is obtained cis-3-(p-dimethylaminophenyl)-2,2-dimethyl-5-(p-methoxyphenyl)-pyrrolidine dihydrochloride, having a melting point of 180° C.

The 2-(p-methoxyphenyl)-5,5-dimethyl-4-(p-dimethylaminophenyl)-1-pyrroline hydrochloride used as the starting material can be prepared as follows:

70 G. of 4'-methoxy-4-methyl-4-nitro-3-(p-dimethylaminophenyl)-valerophenone are dissolved in a mixture of 600 ml. of ethanol and 600 ml. of formic acid. 120 G. of zinc powder are added portionwise to this solution over a period of 30 hours while stirring, the mixture being held at 60° C. during the whole time partly by cooling and partly by heating. The zinc sludge is then filtered off, the filtrate diluted with water and made alkaline with sodium hydroxide while cooling with ice. The mixture is extracted with methylene chloride, the organic phase dried over sodium sulfate and the solvent removed under reduced pressure. The residue is suspended in acetone at 0° C. by intensive stirring. The non-dissolved constituent, 2-(p-methoxyphenyl)-5,5-dimethyl-4-(p-dimethylaminophenyl)-1-pyrroline oxide, is filtered off and the filtrate evaporated under reduced pressure. The residue is taken up in dilute hydrochloric acid and extracted with methylene chloride until the organic phase remains colorless. The aqueous phase is made alkaline with 3-N sodium hydroxide and again extracted with methylene chloride. The organic phase is washed with water and dried over sodium sulfate. After evaporation of the solvent under reduced pressure, there remains an oil which is taken up in ethanolic hydrochloric acid. At −18° C. there crystallizes therefrom 2-(p-methoxyphenyl)-5,5-dimethyl-4-(p-dimethylaminophenyl)-1-pyrroline hydrochloride, having a melting point of 225° C. (decomposition).

The following Examples illustrate typical pharmaceutical preparations provided by the present invention.

EXAMPLE A

Tablets containing the following ingredients are produced:

| | |
|---|---|
| 5-(p-methoxyphenyl)-2,2-dimethyl-3-(2-thienyl)-1-pyrrolidine hydrochloride (active ingredient) | 130.0 mg. |
| Mannitol | 100.0 mg. |
| Maize starch | 145.0 mg. |
| Polyvinylpyrrolidone | 15.0 mg. |
| Talc | 9.0 mg. |
| Magnesium stearate | 1.0 mg. |
| | 400.0 mg. |

The active ingredient is mixed with the mannitol and a portion of the maize starch and sieved. The resulting powder mixture is granulated in the usual manner with the polyvinylpyrrolidone, which is dissolved in a suitable solvent, and dried. The remaining ingredients are then admixed and the resulting mixture is pressed to tablets of appropriate size.

EXAMPLE B

An injection solution is produced by dissolving 130 g. of 5-(p-methoxyphenyl)-2,2-dimethyl-3-(2-thienyl)-1-pyrrolidine hydrochloride in 1 l. of water for injection. The solution is filtered fibre-free while gassing with nitrogen and filled into 1 cm³ ampules, also while gassing with nitrogen. The ampules are sealed and sterilized in a steam autoclave at 120° C. for 20 minutes.

We claim:
1. 5-(p-methoxyphenyl)-2,2-dimethyl-3-(2-thienyl)-pyrrolidine.
2. Cis-5-(p-methoxyphenyl)-2,2-dimethyl-3(2-thienyl)-pyrrolidine.

* * * * *